(12) United States Patent
Bornzin et al.

(10) Patent No.: US 7,711,437 B1
(45) Date of Patent: May 4, 2010

(54) LEAD FIXATION DEVICE

(75) Inventors: Gene A. Bornzin, Simi Valley, CA (US); Yougandh Chitre, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 611 days.

(21) Appl. No.: 11/562,725

(22) Filed: Nov. 22, 2006

(51) Int. Cl.
*A61N 1/00* (2006.01)
(52) U.S. Cl. ..................................... 607/116
(58) Field of Classification Search ............... 607/116
See application file for complete search history.

(56) References Cited

U.S. PATENT DOCUMENTS

| | | | |
|---|---|---|---|
| 5,324,327 | A | 6/1994 | Cohen |
| 5,405,373 | A | 4/1995 | Petersson et al. |
| 5,487,758 | A | 1/1996 | Hoegnelid et al. |
| 5,522,874 | A | 6/1996 | Gates |
| 5,545,201 | A | 8/1996 | Helland et al. |
| 5,728,140 | A | 3/1998 | Salo et al. |
| 6,240,320 | B1 | 5/2001 | Spehr et al. |
| 6,298,272 | B1 | 10/2001 | Peterfeso et al. |
| 6,363,286 | B1 | 3/2002 | Zhu et al. |
| 6,501,994 | B1 * | 12/2002 | Janke et al. ............ 607/127 |
| 2003/0060868 | A1 | 3/2003 | Janke et al. |
| 2003/0220676 | A1 | 11/2003 | Helland |
| 2004/0133259 | A1 | 7/2004 | Janke et al. |
| 2005/0131511 | A1 | 6/2005 | Westlund |
| 2006/0122682 | A1 * | 6/2006 | Sommer et al. ............ 607/127 |

FOREIGN PATENT DOCUMENTS

WO   0057949   10/2000

\* cited by examiner

*Primary Examiner*—George Manuel

(57) ABSTRACT

A lead fixation device that includes a helix having a surface, and a layer of electrically insulating material that covers one or more selected regions of the surface leaving one or more additional regions of the surface exposed. The insulating material defines one of a plurality of individual exposed portions along the length of the helix having a plurality of different configurations, e.g. shapes and sizes, or an insulating strip that wraps around the helix while advancing along the length of the helix.

17 Claims, 5 Drawing Sheets

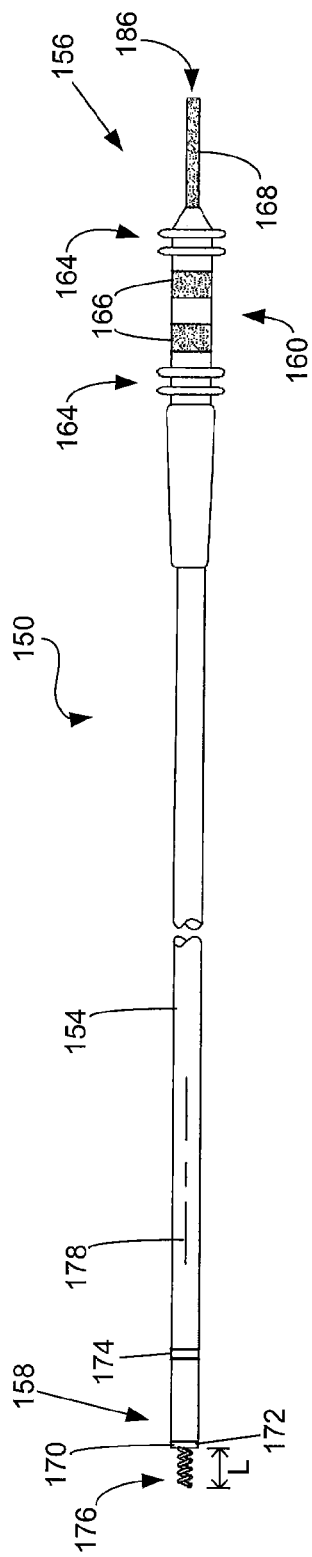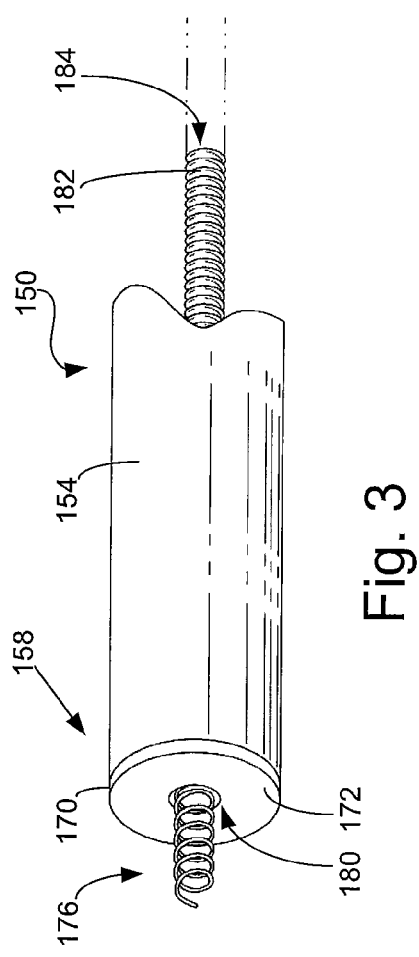

LEAD FIXATION DEVICE

BACKGROUND OF THE INVENTION

1. Technical Field

The invention relates generally to body implantable leads for conducting electrical signals to and from tissue. More specifically, the invention relates to a lead fixation device made of an electrically conductive material that is selectively coated with an electrically insulating material to increase the impedance of the lead fixation device.

2. Background

Many implantable medical devices ("IMDs") use body implantable leads (hereinafter "leads") having one or more electrodes to deliver stimulation pulses to, or sense electrical impulses that are output from, tissue within a patient. An example IMD is a heart stimulation device, e.g., a pacemaker, a cardioverter, a defibrillator, or any other type of stimulating/sensing instruments, which uses one or more leads to deliver electrical stimulation pulses to a heart and to sense electrical impulses generated by the heart. Thus, the leads are used by the IMD to assist in the reversal, via defibrillation or cardioversion, of certain life threatening arrhythmias, or to stimulate, via pacing, the contraction of the heart.

During use, a microcontroller within the IMD interprets electrical signals that are sensed by the electrode(s). In response to the sensed electrical signals, the IMD's microcontroller can decide to pace or shock the heart via transmission of electrical energy from a power source, e.g., a battery, within the IMD through the lead and electrode(s), and into heart tissue. Thus, the lead functions as an electrical conduit through which electrical pulses can be delivered from the IMD to heart tissue and electrical signals that are sensed at the heart tissue can be delivered to the IMD.

Typically, a lead has a proximal end, which is configured to interface with the IMD, and a distal end, which includes the electrode(s) and is configured to contact tissue within the patient. During installation of the IMD and its associated lead(s), the distal end of each lead is inserted through the patient's venous system and into the patient's heart. After it is determined that the distal end of the lead is adjacent to a desired tissue location, a lead fixation device, e.g., a sharpened helix, located at the distal end is used to secure the distal end of the lead to the tissue. The lead fixation device can be made of a conductive material, and the lead fixation device can be electrically coupled to an electrode at the lead distal end. In these instances, the lead fixation device and/or the electrode can be used to emit and sense electrical signals.

When designing a lead electrode and/or lead fixation device that is to be implanted within a patient's body, one of the more important design requirements is that a high value of impedance exists at the interface between the tissue and the electrode and/or the lead fixation device. A high value of impedance at the interface is desirable because it decreases the amount of current necessary for stimulating the tissue, and consequently increases the life span of the IMD power source, e.g., battery, and therefore lengthens the over all life of the IMD.

It should therefore be appreciated that there is a need for a lead that includes a high-impedance lead fixation device that provides the lead with adequate mechanical stability, and does not excessively drain the IMD power, and thus, extends the life of the IMD. The present invention satisfies these needs.

SUMMARY

Certain embodiments described herein include a lead fixation device that has a high value of impedance, which reduces power drain from an IMD battery, and thus, extends the life of the IMD. An exemplary embodiment of the invention is a lead fixation device that includes a helix having a surface, and a layer of electrically insulating material, which covers one or more selected regions of the surface leaving one or more additional regions of the surface exposed. The insulating material defines one of the following: a plurality of individual exposed portions along the length of the helix having a plurality of different configurations; and an insulating strip that wraps around the helix while advancing along the length of the helix.

In other, more detailed features, the lead fixation device has an impedance of at least 750 ohms, or an impedance in a range from approximately 750 ohms to approximately 1,500 ohms. Also, the helix can be made of an electrically conductive noble metal such as a platinum-iridium alloy, an alloy consisting of approximately 90 percent platinum and approximately 10 percent iridium, or an alloy consisting of approximately 80 percent platinum and approximately 20 percent iridium. In addition, the electrically insulating material can be silicone, polyurethane, copolymer, polymer, fluoropolymer, ethylene tetrafluoroethylene, or polytetrafluoroethylene.

In other, more detailed features, the layer of electrically insulating material has a thickness of at least 1.0 microns, or a thickness in a range from approximately 1.0 microns to approximately 2.5 microns. Also, the lead fixation device can have one of the following features: the helix has a length in a range from approximately 1.2 millimeters to approximately 2.2 millimeters, the surface of the helix has a total area in a range from approximately 5.0 millimeters$^2$ to approximately 8.5 millimeters$^2$, and the one or more additional regions of the surface that are exposed have a combined area in a range from approximately 2.0 millimeters$^2$ to approximately 5.0 millimeters$^2$. In addition, the surface of the helix can have a total area, and the electrically insulating material can cover from approximately 40 percent to approximately 80 percent of the total area.

In another exemplary embodiment, a lead has a distal end where the previously discussed lead fixation device is located. In other, more detailed features of the invention, the lead can include an electrode that is located at the distal end and is electrically coupled to the lead fixation device. The lead can further include a proximal end, a connector assembly, which is located at the proximal end and is adapted to interface with an IMD, and a conductor, which is electrically coupled between the lead fixation device and the connector assembly. Also, the IMD can be a pacemaker, a defibrillator, a cardioverter, a neurostimulation device, or a gastric stimulation device. In addition, the lead can be adapted to be implanted within a patient's body. Furthermore, the distal end can be adapted to be coupled to tissue within the patient's heart using the lead fixation device.

Another exemplary embodiment is a method for creating a lead fixation device from an electrically insulating material and a helix, which has a surface. The method includes depositing the electrically insulating material over at least a part of the surface, and removing one or more portions of the electrically insulating material from the surface so the remaining insulating material defines one of: a plurality of individual exposed portions along the length of the helix having a plurality of different configurations, and an insulating strip that wraps around the helix while advancing along the length of the helix.

In other, more detailed features of the invention, depositing the electrically insulating material on the surface of the helix is accomplished using electrophoretic deposition, dip coating, spin coating, in situ polymerization, vapor deposition, or sputtering. Also, when the electrically insulating material is oriented spirally along the helix, removing a portion of the electrically insulating material can be accomplished using laser ablation.

Other features of the invention should become apparent from the following description of the preferred embodiments taken in conjunction with the accompanying drawings, which illustrate, by way of example, the principles of the invention, and depict objects that are not necessarily drawn to scale.

BRIEF DESCRIPTION OF THE DRAWINGS

FIG. 2 is a side view of a lead including a lead fixation device.

FIG. 3 is a perspective view of a distal end of the lead of FIG. 2.

DETAILED DESCRIPTION

Figure 1:
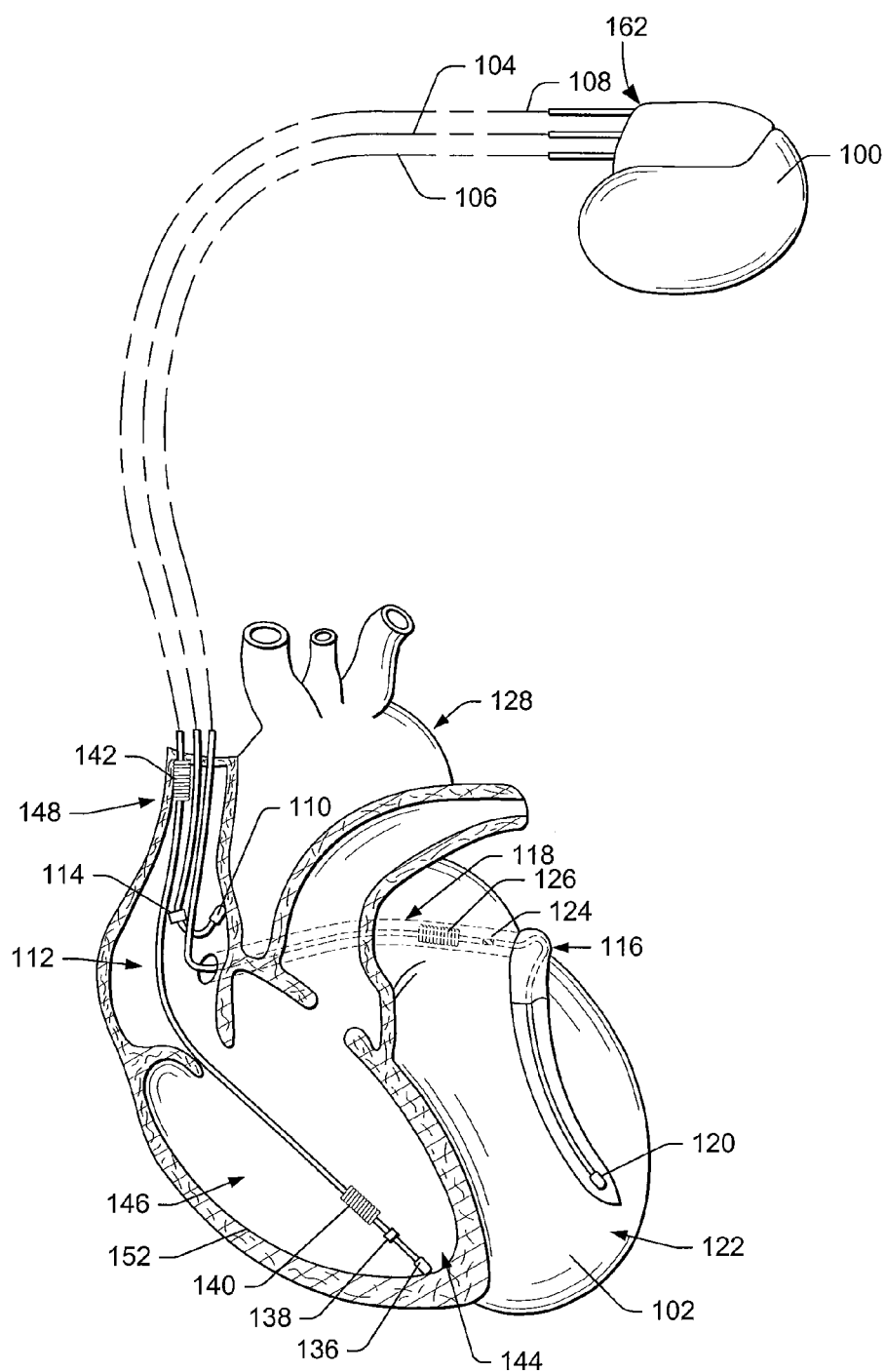
FIG. 1 is a simplified diagram illustrating an IMD embodying the present invention, which is electrically coupled to three leads that are positioned within a heart.

Although the invention can be used in conjunction with a wide variety of IMDs, e.g., neurostimulation devices or gastric stimulation devices, with reference now to the illustrative drawings, and particularly to FIG. 1, there is shown an exemplary IMD 100, a heart stimulation device, e.g., a pacemaker, a defibrillator, and/or a cardioverter, in electrical communication with a patient's heart 102 by way of three leads 104, 106, and 108, which are suitable for delivering multi-chamber stimulation and shock therapy. To sense atrial cardiac signals and to provide right atrial chamber stimulation therapy, the IMD is coupled to an implantable right atrial lead 104 having at least an atrial tip electrode 110, which typically is implanted in contact with the patient's right atrium 112. As shown in FIG. 1, the right atrial lead 104 also includes a right atrial ring electrode 114.

To sense left atrial and ventricular cardiac signals and to provide left chamber pacing therapy, the IMD 100 is coupled to a coronary sinus lead 106, which is designed for placement in the coronary sinus region 116 via the coronary sinus 118, and for positioning a distal electrode 120 adjacent to the left ventricle 122 and/or additional electrode(s) 124 and 126 adjacent to the left atrium 128. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, an exemplary coronary sinus lead is designed to receive atrial and ventricular cardiac signals and to deliver left ventricular pacing therapy using at least a left ventricular tip electrode 120, left atrial pacing therapy using at least a left atrial ring electrode 124, and shocking therapy using at least a left atrial coil electrode 126.

In FIG. 1, the IMD 100 also is shown in electrical communication with the patient's heart 102 by way of an implantable right ventricular lead 108 having, in this implementation, a right ventricular tip electrode 136, a right ventricular ring electrode 138, a right ventricular coil electrode 140, and a superior vena cava ("SVC") coil electrode 142. Typically, the right ventricular lead 108 is inserted into the heart to place the right ventricular tip electrode 136 proximate the right ventricular apex 144 so that the right ventricle coil electrode 140 is positioned in the right ventricle 146 and the SVC coil electrode 142 is positioned in the superior vena cava 148. Accordingly, the right ventricular lead 108 is capable of sensing or receiving cardiac signals, and delivering stimulation in the form of pacing and shock therapy to the right ventricle 146.

The IMD 100 can be configured to treat both fast and slow arrhythmias with stimulation therapy, including cardioversion, defibrillation, and pacing stimulation in the appropriate chamber(s) 112, 122, 128, and 146 of the heart 102. While a particular multi-chamber device is shown in FIG. 1, it is to be appreciated and understood that this is done for illustration purposes only. Thus, the techniques and methods described below can be implemented in connection with any suitably configured or configurable IMD.

According to preferred embodiments of the present invention, an example lead 150 is shown in FIGS. 2 and 3. The lead 150 is configured (herein also referred to as "adapted") to be an electrical link between the IMD 100 and tissue 152 (FIG. 1) within the heart 102 that is to be electrically stimulated. The lead 150 includes a tubular sheath 154 that extends between a proximal end 156 and a distal end 158. The proximal end 156 includes a connector assembly 160 that is tubular in shape and configured to interface both electrically and mechanically with the IMD via a receptacle 162 (FIG. 1) in the IMD 100. The connector assembly 160 includes two spaced apart pairs of seals 164 in accordance with well known arrangements in the art, which prevent the leakage of body fluids into the IMD when the connector assembly is interfaced with the IMD receptacle 162. The connector assembly 160 also includes a pair of ring terminal contacts 166 and a rotatable pin terminal 168.

The distal end 158 includes a distal tip 170 having at least one electrode 172, e.g., the atrial tip electrode 110 (FIG. 1), the left ventricular tip electrode 120, or the right ventricular tip electrode 136. The lead 150 also can include a ring electrode 174, e.g., the right atrial ring electrode 114 (FIG. 1) or the right ventricular ring electrode 138, near the distal end. The distal end 158 of the lead also includes a lead fixation device 176 in the form of a sharpened, electrically conductive helix, which is aligned along a longitudinal axis 178 of the lead, configured to be extended or retracted through an aperture 180 that is formed in the distal end, and can be electrically coupled to the electrode 172.

The sheath 154 is made of a biocompatible insulating material, e.g., silicone rubber, polyurethane, fluorinated resin, or other like material. The sheath protects a helically wound conductor 182, which is located within the sheath, from contact with patient body fluids and tissue. Typically, the helically wound conductor 182 is a multi-filar coil made of a conductive metal, e.g., a platinum-iridium alloy. At the proximal end 156 of the lead 150, the conductor 182 is electrically coupled to one of the ring terminal contacts 166, and at the distal end 158, the conductor is electrically coupled to the electrode 172 and/or the lead fixation device 176, for example, by way of spot welds or laser welds.

The helically wound conductor 182 forms a cylindrical envelope or tube 184, which commonly is referred to as the lumen. The lumen is configured to receive a stylet (not shown), which also is referred to as a guidewire, during the installation of the lead 150 into the patient. During use, the stylet is inserted into the lumen through a bore 186 in the connector assembly 160, and the stylet is used to stiffen, advance, and manipulate the lead during insertion of the lead into the patient's venous system, e.g., through the patient's subclavian vein, and into one or more chambers 112 and 146 of the heart.

During the installation of the lead, fixation device 176 is maintained in a retracted position within the lead 150 until the electrode 172 is brought into contact with a desired endocardial tissue location. Because the lead fixation device is retracted within the lead during lead insertion into the venous system and heart 102 (FIG. 1), the lead fixation device is prevented from unintentionally engaging and damaging tissue 152 as the lead is advanced.

The lead fixation device 176 is used to secure the distal end 158 of the lead 150 and the electrode 172 in contact with endocardial heart tissue 152 (FIG. 1) after the electrode is adjacent a location of interest within the heart 102. In particular, the lead fixation device is configured to be screwed into the tissue of the heart in a conventional manner. During the installation process, a medical practitioner can use the stylet (not shown) to extend and rotate the lead fixation device so that it pierces and engages the heart tissue.

In one embodiment, the medical practitioner rotates the stylet (not shown) in one direction (either clockwise or counterclockwise), which, in turn, causes the lead fixation device 176 to rotate as it extends through the aperture 180. By turning the stylet in the opposite direction, the medical practitioner can cause the lead fixation device to disengage the heart tissue 152 (FIG. 1) and retract back into the lead 150 via the aperture. In another embodiment, the medical practitioner can extend the lead fixation device 176 through the aperture 180 and secure the distal end 158 of the lead to the heart tissue by applying a torque to the rotatable pin terminal 168 at the lead's proximal end 156 without the use of the stylet. Also, in this embodiment, the medical practitioner can disengage the lead fixation device 176 from the heart tissue and retract the lead fixation device into the aperture 180 by applying a torque to the lead's proximal end in the opposite direction.

After the lead 150 is positioned securely in a desired location, the stylet (if used) is removed from the lead and discarded, and the connector assembly 160 is inserted into the IMD's receptacle 162 (FIG. 1). Next, the medical practitioner creates a pocket (not shown) beneath the patient's skin in the upper portion of the patient's chest to hold the IMD 100, the IMD is implanted within the pocket, and the medical practitioner sutures the pocket closed.

As previously stated, it is desirable to develop high-impedance leads since such leads tend to extend the life of the IMD. The impedance value of a lead 150 that includes an electrode 172, which may be electrically coupled to a conductive lead fixation device 176, is directly proportional to the conductive surface area of the electrode and/or the conductive surface area of the lead fixation device. One method for increasing lead impedance is to reduce the size of the electrode 172 and/or the lead fixation device 176. This, however, would most likely adversely impact the mechanical and thereby electrical stability of the lead. For stable mechanical and electrical performance of the lead, the electrode 172 and lead fixation device 176 must be large enough to provide adequate mechanical stability to mitigate dislodgement from the tissue 152, and, at the same time, provide for high impedance to mitigate the power losses due to the drainage of battery current from the IMD 100. These are two rather conflicting requirements.

Figure 4:
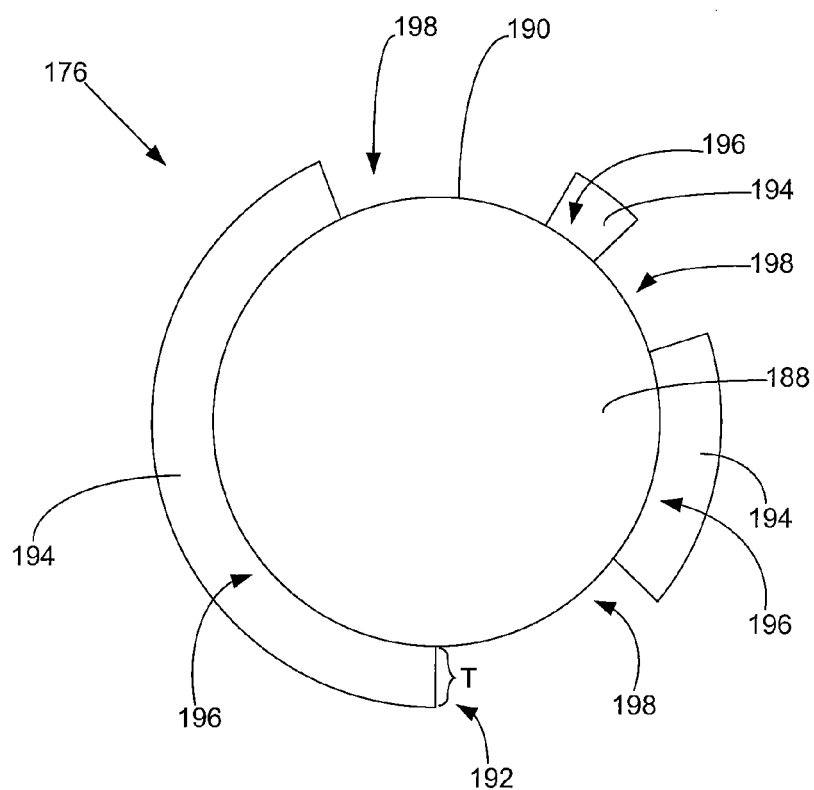
FIG. 4 is a cross-sectional view of a lead fixation device according to a preferred embodiment.
Figure 5:
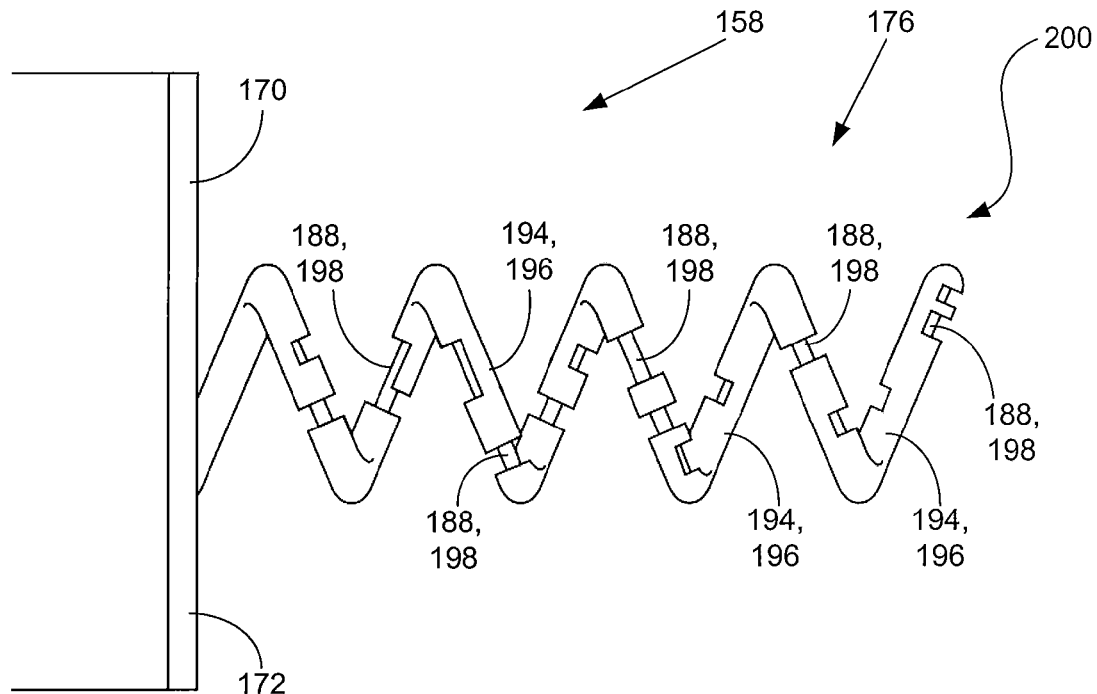
FIG. 5 is a side view of a distal end of a lead including a lead fixation device according to an embodiment.
Figure 6:
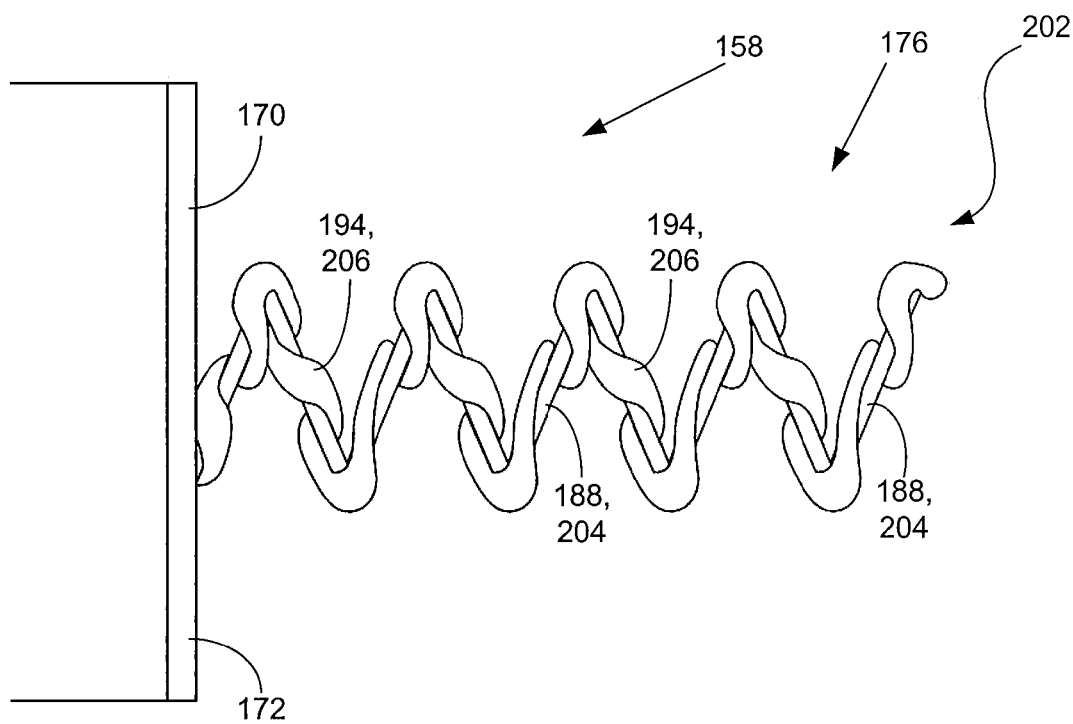
FIG. 6 is a side view of a distal end of a lead including a lead fixation device according to another embodiment.

According to embodiments of the present invention and referring additionally to the cross-sectional view of an embodiment of a lead fixation device 176 shown in FIG. 4 and the side views of embodiments of lead fixation devices shown in FIGS. 5 and 6, the lead fixation device includes a helix 188 that is resistant to corrosion from body fluids. The helix 188 is made of low-resistance, electrically conductive, biocompatible material such as a noble metal, e.g., a platinum-iridium alloy, for example, a platinum-iridium alloy consisting of approximately 90 percent platinum and approximately 10 percent iridium, or a platinum-iridium alloy consisting of approximately 80 percent platinum and approximately 20 percent iridium.

In example embodiments of the lead fixation device, the helix has a length "L" (FIG. 2) in a range from approximately 1.2 millimeter to approximately 2.2 millimeter, and a surface 190 that has a total surface area in a range from approximately 5.0 millimeter$^2$ to approximately 8.0 millimeter$^2$. Also, the helix is partially coated with a layer 192 of a biocompatible and electrically insulating material 194, which conforms to the conductive surface of the helix and covers one or more selected regions 196 of the surface of the helix leaving one or more additional regions 198 of the surface exposed. Examples of the electrically insulating material include the following: silicone, polyurethane, copolymer, and/or polymer, e.g., a fluoropolymer such as ethylene tetrafluoroethylene ("ETFE") or polytetrafluoroethylene ("PTFE").

During manufacturing, at least a part of, if not all of, the helix 188 is coated with a thin layer 192 of the electrically insulating material 194 using any convenient process, for example, electrophoretic deposition, dip coating, spin coating, in situ polymerization, vapor deposition, or sputtering. Preferably the electrically insulating material is deposited on the conductive surface of the helix in a layer having a thickness "T" that increases the impedance of the lead fixation device 176 without interfering with the mechanical operation of the lead fixation device. For example, the thickness "T" of the electrically insulating material should be at least 1.0 microns or greater, and usually between approximately 1.0 microns and approximately 2.5 microns.

After the electrically insulating material 194 is deposited onto the helix 188, portions of the layer 192 of electrically insulating material are removed resulting in one or more exposed regions 198 of the underlying conductive surface 190. The portions of the layer of electrically insulating material can be removed using various techniques, such as laser ablation.

The size, shape, and number of exposed regions 198 on the surface 190 can vary depending upon the technique that is used to remove the electrically insulating material 194 from the helix 188. For example, for the embodiment of the lead fixation device 176 that has a length "L" (FIG. 2) in a range from approximately 1.2 millimeters to approximately 2.2 millimeters and a total surface area in a range from approximately 5.0 millimeters$^2$ to approximately 8.5 millimeters$^2$, the total exposed surface area, which is made up of individual exposed regions 198, can be in a range from approximately 2.0 millimeters$^2$ and 5.0 millimeters$^2$.

Referring additionally to FIG. 5, in an example embodiment 200, the exposed regions 198 of the helix 188 are relatively small in area and are separated from one another by regions 196 that are covered with insulating material 194. The configuration, e.g., shape and size, of these exposed regions 198 are preferably non-uniform. For example, some of the exposed regions 198 may extend completely around the circumference of the helix 188, while others may only extend partially around the helix. Also, the size or length of the exposed regions 198 may vary. In this embodiment, the exposed regions 198 typically are formed by ablating the insulating material from the helix surface 190.

Referring additionally to FIG. 6, in an additional example embodiment 202, when viewed from the side, the exposed regions 188 form one or more strip-like areas 204 that are separated by strip-like areas 206 of electrically insulating material that are oriented along the length "L" (FIG. 2) of the helix, meaning that the strip-like areas of electrically insulating material are directed along the length of the helix. Described another way, the continuum of strip-like areas 206 along the length of the helix 188 form an electrically insulating strip that wraps or winds around the helix, while advancing along the length of the helix. The exposed regions 204 form multiple stimulation surfaces on the lead fixation device 176. Thus, the lead fixation device 176 includes a plurality of exposed conductive regions 204 that have a combined area that is less than the total surface area of the helix.

Figure 7:
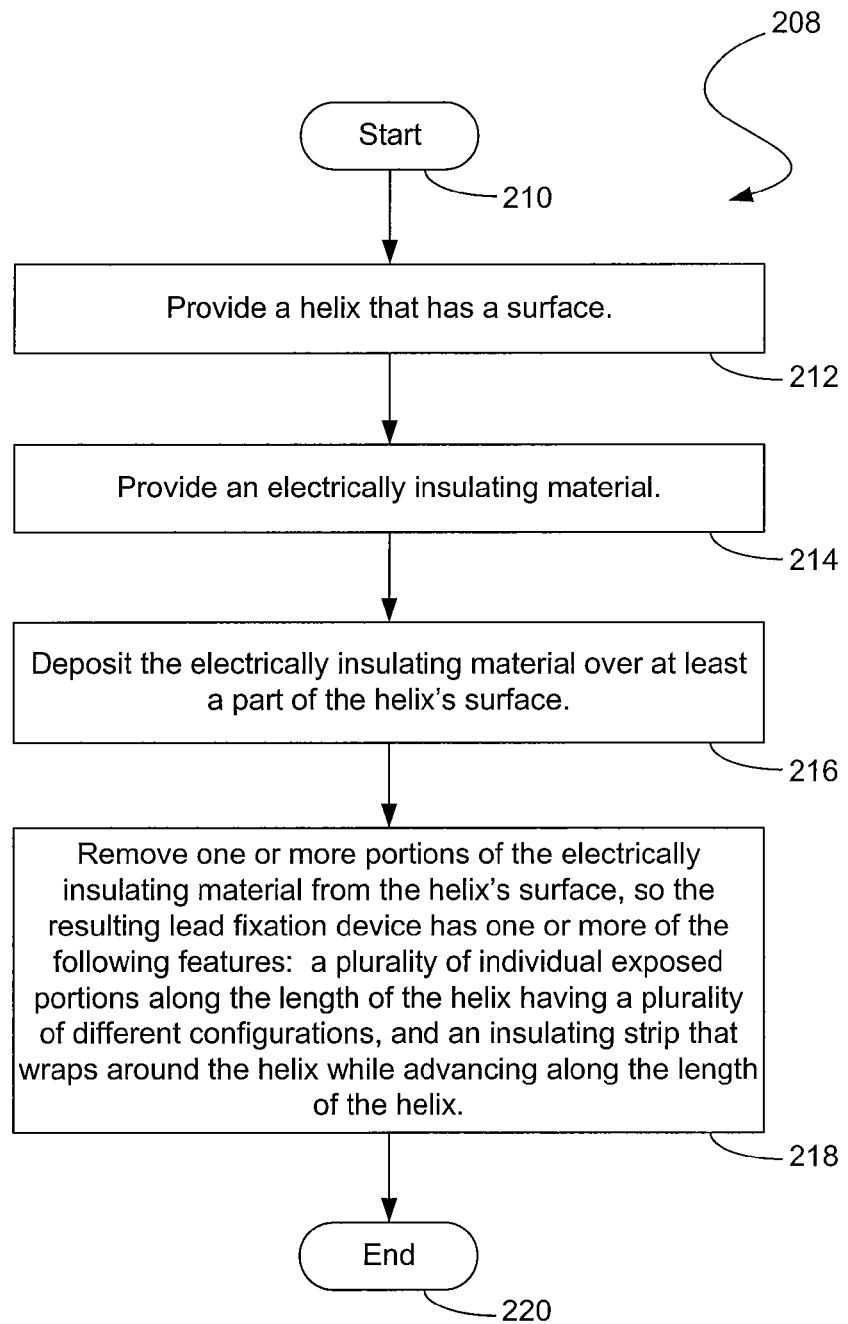
FIG. 7 is a flow diagram of an example method for creating a lead fixation device.

FIG. 7 is a flowchart that shows an example method 208 for creating embodiments of the lead fixation device 176. The method starts at step 210. Next, at step 212, a helix 188 that has a surface 190 is provided, and at step 214, an electrically insulating material 194 is provided. Next, at step 216, the electrically insulating material is deposited over at least a part of the surface. At step 218, one or more portions of the electrically insulating material is removed from the helix surface so the resulting lead fixation device has one or more of the following features: the one or more portions of the electrically insulating material were removed from the surface using an ablation technique, and the electrically insulating material is oriented along the helix. The method ends at step 220.

The layer 192 of electrically insulating material 194 that covers the helix 188 substantially reduces the area of conductive surface of the helix that contacts the heart tissue 152 after the lead 150 is implanted. In fact, the impedance of the lead fixation device 176 is proportional to the amount of the helix surface area that is exposed. More specifically, the impedance of the lead fixation device 176 increases in value as the proportion of the exposed surface area decreases. In embodiments, the layer of electrically insulating material covers from approximately 40 percent to approximately 80 percent of the total surface area of the helix, resulting in a lead fixation device having an impedance value that typically is greater than approximately 750 ohms, and can range from approximately 750 ohms to approximately 1,500 ohms. Stated otherwise, the total exposed surface areas of the helix may be in the range from approximately 20 percent and 60 percent.

Advantageously, embodiments of the present invention include lead fixation devices 176 that are fabricated to be mechanically stable and to have high values of impedance, and thus can be used to minimize the amount of current used to stimulate heart tissue 152. As a result, the lead fixation devices 176 can be used to reduce battery power consumption and thereby prolong the life of the IMD 100. Also, because the design of the lead fixation device prolongs the life of the IMD 100, the design of the lead fixation device also results in less frequent surgical procedures for the patient.

The foregoing detailed description of the present invention is provided for purposes of illustration, and it is not intended to be exhaustive or to limit the invention to the particular embodiments disclosed. The embodiments may provide different capabilities and benefits, depending on the configuration used to implement the key features of the invention. Accordingly, the scope of the invention is defined only by the following claims.

What is claimed is:

1. A lead fixation device comprising:
    a conductive material in the form of a wire having a length, circumference and surface, the wire configured as a helix defining a lumen, the helix having an outer surface area facing away from the lumen and an inner surface area facing toward the lumen; and
    a layer of electrically insulating material that covers one or more selected regions of the wire leaving one or more additional regions of the wire exposed to thereby define one of the following:
        a plurality of individual exposed portions of wire along the length of the wire having a plurality of different configurations, the plurality of configurations comprising an exposed portion that extends completely around the circumference of the wire, an exposed portion on the outer surface of the helix opposite an insulated region on the inner surface of the helix, and an exposed portion on the inner surface of the helix opposite an insulated region on the outer surface of the helix; and
        an insulating strip that wraps around the circumference of the wire while advancing along the length of the wire so as to create exposed portions on the outer surface area of the helix opposite insulated regions on the inner surface of the helix, and exposed portions on the inner surface area of the helix opposite insulated regions on the outer surface of the helix.

2. The lead fixation device of claim 1, wherein the lead fixation device has an impedance of at least 750 ohms.

3. The lead fixation device of claim 1, wherein the surface of the wire has a total area and the combined surface area of the exposed portions is in a range from approximately 20 percent to 60 percent of the total surface area.

4. The lead fixation device of claim 1, wherein the wire is made of a noble metal selected from the group consisting of a platinum-iridium alloy, an alloy consisting of approximately 90 percent platinum and approximately 10 percent iridium, and an alloy consisting of approximately 80 percent platinum and approximately 20 percent iridium.

5. The lead fixation device of claim 1, wherein the electrically insulating material is selected from the group consisting of silicone, polyurethane, copolymer, polymer, fluoropolymer, ethylene tetrafluoroethylene, and polytetrafluoroethylene.

6. The lead fixation device of claim 1, wherein the layer of electrically insulating material has a thickness of at least 1.0 microns.

7. The lead fixation device of claim 1, wherein the lead fixation device has at least one of the following features:
    the helix has a length in a range from approximately 1.2 millimeters to approximately 2.2 millimeters;
    the surface of the wire has a total area in a range from approximately 5.0 millimeters$^2$ to approximately 8.5 millimeters$^2$; and
    the one or more additional regions of the surface that are exposed have a combined area in a range from approximately 2.0 millimeters$^2$ to approximately 5.0 millimeters$^2$.

8. The lead fixation device of claim 1, wherein:
    the surface of the wire has a total area; and the electrically insulating material covers from approximately 40 percent to approximately 80 percent of the total area.

9. A lead having a distal end, the lead comprising:
a lead fixation device that is located at the distal end and includes:
a conductive material in the form of a wire having a length, circumference and surface, the wire configured as a helix defining a lumen, the helix having an outer surface area facing away from the lumen and an inner surface area facing toward the lumen, and
a layer of electrically insulating material that covers one or more selected regions of the wire leaving one or more additional regions of the wire exposed to thereby define one of the following:
a plurality of individual exposed portions of wire along the length of the wire having a plurality of different configurations, the plurality of configurations comprising an exposed portion that extends completely around the circumference of the wire, an exposed portion on the outer surface of the helix opposite an insulated region on the inner surface of the helix, and an exposed portion on the inner surface of the helix opposite an insulated region on the outer surface of the helix; and
an insulating strip that wraps around the circumference of the wire while advancing along the length of the wire so as to create exposed portions on the outer surface area of the helix opposite insulated regions on the inner surface of the helix, and exposed portions on the inner surface area of the helix opposite insulated regions on the outer surface of the helix.

10. The lead of claim 9, wherein the lead fixation device has an impedance of at least 750 ohms.

11. The lead of claim 9, wherein the surface of the wire has a total area and the combined surface area of the exposed portions is in a range from approximately 20 percent to 60 percent of the total surface area.

12. The lead of claim 9, wherein the lead fixation device has a feature selected from the group consisting of:
the layer of electrically insulating material has a thickness of at least 1.0 microns;
the helix has a length in a range from approximately 1.2 millimeters to approximately 2.2 millimeters;
the surface of the wire has a total area in a range from approximately 5.0 millimeters$^2$ to approximately 8.5 millimeters$^2$; and
the one or more additional regions of the surface that are exposed have a combined area in a range from approximately 2.0 millimeters$^2$ to approximately 5.0 millimeters$^2$.

13. The lead of claim 9, further comprising an electrode that is located at the distal end and is electrically coupled to the lead fixation device.

14. The lead of claim 9, further comprising:
a proximal end;
a connector assembly that is located at the proximal end and is adapted to interface with an implantable medical device; and
a conductor that is electrically coupled between the lead fixation device and the connector assembly.

15. The lead of claim 14, wherein the implantable medical device comprises one of a pacemaker, a defibrillator, a cardioverter, a neurostimulation device, and a gastric stimulation device.

16. The lead of claim 9, wherein the lead is adapted to be implanted within a patient's body.

17. The lead of claim 9, wherein the distal end is adapted to be coupled to tissue within a patient's heart using the lead fixation device.

* * * * *